US006869774B2

(12) United States Patent
Endo et al.

(10) Patent No.: US 6,869,774 B2
(45) Date of Patent: Mar. 22, 2005

(54) METHODS OF SYNTHESIZING CELL-FREE PROTEIN

(75) Inventors: Yaeta Endo, 478-17, Kumanodai, Matsuyama-shi, Ehime 791-8016 (JP); Tatsuya Sawasaki, Matsuyama (JP); Tomio Ogasawara, Iyo (JP)

(73) Assignee: Yaeta Endo, Ehime (JP)

( * ) Notice: Subject to any disclaimer, the term of this patent is extended or adjusted under 35 U.S.C. 154(b) by 61 days.

(21) Appl. No.: 10/344,803

(22) PCT Filed: Aug. 28, 2001

(86) PCT No.: PCT/JP01/07356

§ 371 (c)(1),
(2), (4) Date: Mar. 18, 2003

(87) PCT Pub. No.: WO02/24939

PCT Pub. Date: Mar. 28, 2002

(65) Prior Publication Data

US 2003/0162246 A1 Aug. 28, 2003

(30) Foreign Application Priority Data

Aug. 29, 2000 (JP) ........................................ 2000-259186

(51) Int. Cl.[7] .................................................. C12P 21/06
(52) U.S. Cl. ...................... 435/68.1; 435/69.1; 530/350; 424/184
(58) Field of Search ............................... 435/68.1, 69.1, 435/172.3; 536/23.1; 530/350; 424/184

(56) References Cited

U.S. PATENT DOCUMENTS 5,478,730 A * 12/1995 Alakhov et al. ............ 435/68.1

FOREIGN PATENT DOCUMENTS

| JP | 1080295 A1 * | 3/1988 | |
| JP | 10-80295 | 3/1998 | ........... C12P/21/00 |
| WO | WO 00/68412 | 11/2000 | ........... C12P/21/00 |
| WO | WO 01/27260 A1 | 4/2001 | ........... C12N/15/10 |

OTHER PUBLICATIONS

Shuilliang Yao, A Novel Method of High Yield Cell–Free Protein Synthesis, Sep. 1997, Journal of Fermentation and Bioengineering, vol. 84, No. 6 548–552.*

* cited by examiner

*Primary Examiner*—Robert A. Wax
*Assistant Examiner*—Robert B. Mondesi
(74) *Attorney, Agent, or Firm*—Kilyk & Bowersox, PLLC

(57) ABSTRACT

One embodiment of the present invention is a diffusion continuous batch cell-free protein-synthesis method characterized simultaneously by continuously supplying substrate and energy source molecules in the supply phase to the reaction phase by the free diffusion via interface between both phases and by transferring by-products formed in the reaction phase by enhancing the efficiency of the synthesis reaction by prolonging the reaction lifetime by directly contacting a synthesis reaction mixture (reaction phase) containing a biological extract with a substrate- and energy source-supplying solution (supply phase) without using barrier such as semi-permeable membrane or ultrafiltration membrane in a general cell-free protein-synthesis reaction means. Another embodiment of the present invention is a dilution batch cell-free protein synthesis method characterized by enhancing the efficiency of the protein synthesis by prolonging the reaction lifetime by adding a diluting solution to the reaction mixture after pre-incubating the reaction mixture in a cell-free protein-synthesis reaction means using a wheat-embryo extract. Another embodiment of the present invention is a method characterized by enhancing the efficiency of the synthesis reaction simultaneously by re-supplying substrate and energy sources necessary for the protein synthesis (e.g., amino acids, ATP, GTP, creatine phosphate) to the reaction mixture using a gel filtration column and/or semipermeable membrane and by discontinuously removing by-products formed during the reaction after the synthesis reaction stops in the batch cell-free protein synthesis method.

8 Claims, 6 Drawing Sheets

(A) Protein synthesis as measured by incorporation of amino acid (B) Autoradiogram of synthesis products (A) Protein synthesis as measured by incorporation of amino acid (B) SDS polyacrylamide gel electropherogram of synthesis products (A) Protein synthesis as measured by incorporation of amino acid (B) Autoradiogram of synthesis products

METHODS OF SYNTHESIZING CELL-FREE PROTEIN

This application claims the benefit of earlier filed International Application No. PCT/JP01/07356 filed Aug. 28, 2001.

This application claims priority from Japanese Patent Application No.2000-259186 which is incorporated herein by reference.

1. Technical Field

The present invention relates to a method for synthesizing a protein using a cell-free system.

2. Background Art

At present near the completion of the genome project, the center of the research subject has rapidly been shifting from the gene structural analysis to the gene functional analysis. It is believed that an intracellular protein does not function singly, but expresses its function cooperatively interacting with various protein factors, nucleic acids, low-molecular species, and cell-membrane components, to biologically function as the sum of their interactions.

One of main subjects in the post-genome project is to analyze the relation between structure and function of various protein factor complexes. Results obtained from the analyses are expected to provide very important knowledges in wide areas covering basic biological studies including structural biology and biochemistry, elucidation of the relation between the gene translation product and the etiology in the medical field, and the development of medicines.

As a method for carrying out in vitro the protein-synthesis reaction, so-called "method for cell-free protein synthesis" or the like has been studied actively (Japan Patent Laid-Open Hei 6-98790, Japan Patent Laid-Open Hei 6-225783, Japan Patent Laid-Open Hei 7-194, Japan Patent Laid-Open Hei 9-291, Japan Patent Laid-Open Hei 7-147992) such as a method in which components containing ribosome or the like that is an intracellular original protein-translating device are extracted from an organism, and a translation template, amino acids as substrate, energy sources, various ions, a buffer, and other effective factors are added to the extract to synthesize a protein in vitro.

A cell extract or biological tissue extract for cell-free protein synthesis used for the cell-free protein synthesis system is prepared using *Escherchia coli*, wheat embryo, and rabbit reticulocyte as a raw material. The cell-free protein-synthesis system maintains the performance comparable to the living cell with respect to "the peptide synthesis rate" and "the accuracy of the translation reaction". In addition, the system does not require any complex chemical reaction step or cell-culturing step. Because of these advantages, practical systems for this system have been developed. However, in general, a cell extract obtained from cells of an organism has an extremely unstable protein-synthesis ability, so that a protein-synthesis efficiency was low. In addition, the quality of the cell-free extract during storage was rapidly deteriorated, so that the amount synthesized by a cell protein-synthesis system was as small as the level that can be detected by the radio isotope labelling or the like. As a result, this system could not be used as a practical means for synthesizing a protein.

The applicants provided the following methods for solving faults of the conventional cell-free protein-synthesis system before this application:
1) cell extract pharmaceutical preparation for cell-free protein-synthesis and method for cell-free protein synthesis (WO00/68412), and
2) template molecule that can be widely used and has an efficient function and method for cell-free protein-synthesis system using the same (WO01/27260).

In addition, a device that carries out the continuous synthesis of a cell-free protein for enhancing the efficiency of the protein synthesis. Conventional devices for continuous cell-free protein-synthesis apparatus include the ultrafiltration method, the dialysis membrane method, and the column chromatography method using a column prepared by fixing a translation template on a resin [Spirin, A., et al., (1993) Methods in Enzymology, 217, 123–142]. In particular, the ultrafiltration method and the dialysis membrane method require only simple handling, so that they are widely used.

However, these continuous methods using these membranes have the following problems to solve:
1) the material strength of a membrane for use is low,
2) the membrane performance can be lowered by the clogging, and
3) the operation is complex, so that a skillful technique is necessary.

In addition, the continuous cell-free protein-synthesis method manually using the ultrafiltration membrane method or the dialysis membrane method can be applied to the protein synthesis from a small number of genes, and it was difficult to efficiently perform the protein production from a large number of genes. Thus, the development of the high-throughput full-automatic protein-synthesizing system, for polyspecimen, which permits efficiently carrying out the protein production from a large number of genes is desired, and the development of a new technology in which faults of the conventional continuous cell-free protein-synthesis method are solved is a pressing need.

DISCLOSURE OF THE INVENTION

According to an aspect of the present invention there is provided a cell-free protein-synthesis method using a diffusion continuous batch system that includes a synthesis reaction mixture reaction phase) containing a biological extract and a supply solution (supply phase) containing substrates and energy sources, the method comprising the steps of:
1) bringing the two phases into direct contact with each other to cause a free diffusion via the direct contact interface between the two phases, and continuously supplying substrates and energy source molecules in the supply phase to a translation reaction system in the reaction phase;
2) removing by-products formed in the reaction phase; and
3) thereby prolonging the lifetime of the synthesis reaction, and enhancing the efficiency of the synthesis reaction.

The present invention provides the cell-free protein-synthesis method wherein the biological extract is a wheat-embryo extract.

The present invention provides the cell-free protein-synthesis method wherein the biological extract is an *Escherichia coli* extract.

The scope of the present invention provides the cell-free protein-synthesis method wherein by-products formed in the reaction phase are diluted/removed by transferring to the supply phase.

The scope of the present invention covers the cell-free protein-synthesis method wherein the direct interface formed between the reaction phase and the supply phase is a vertical plane.

According to another aspect of the present invention there is provided a cell-free protein-synthesis method comprising the steps of pre-incubating a cell-free protein-synthesis reaction mixture containing a wheat-embryo extract; and thereafter adding a substrate and energy source-supplying solution to dilute the cell-free protein-synthesis reaction mixture containing a wheat-embryo extract.

According to a further aspect of the present invention there is provided a batch cell-free protein-synthesis method comprising the steps of:

1) treating a reaction mixture after the completion of the synthesis reaction with a gel-filtration column or a semipermeable membrane;
2) re-supplying raw materials and energy sources such as amino acids, ATP, GTP, and creatine phosphate which are necessary for the protein synthesis;
3) simultaneously with the re-supply, removing by-products formed during the reaction from the reaction mixture; and
4) enhancing the efficiency of the reaction by the removal and the re-supply.

BRIEF DESCRIPTION OF DRAWINGS

FIG. 2A illustrates the protein synthesis as measured by $^{14}$C-leucine incorporation with Y-axis being an amount of protein synthesized; X-axis an incubation time. The protein synthesis was carried out by the conventional batch method (○-○), the diffusion continuous batch method (multi-layered method) using a reaction vessel having a bore of 7 mm (□-□, large symbol), 5 mm (□-□, middle symbol), or 3 mm (□-□, small symbol, or the dilution batch method (■-■). The Radioactivity count (Y-axis) showing the amount of protein synthesized was shown per the same volume of a wheat embryo extract. FIG. 2B illustrates an autoradiogram of synthetic products.

FIG. 3A illustrates the protein synthesis as measured by $^{14}$C-leucine incorporation by the conventional batch-type method (○-○) or the diffusion continuous batch method (multi-layered method) using a reactor having a bore of 7 mm (■-■). The radioactivity count (Y-axis) showing the amount of protein synthesized was expressed per the same volume of the embryo extract. FIG. 3B illustrates an SDS-polyacrylamide-gel electropherogram of synthesis products stained by Coomassie Brilliant Blue.

FIG. 4A illustrates the protein synthesis as measured by $^{14}$C-leucine incorporation by the conventional batch method (○-○), the diffusion continuous batch method (multi-layered method) using a reactor vessel having a bore of 7 mm (■-■), or the dilution batch cell-free protein synthesis method (□-□) with Y-axis being the radioactivity count showing the amount of protein synthesized per the same volume of *Escherichia coli* extract. FIG. 4 (B) illustrates an autoradiogram of synthesis products.

BEST MODE FOR CARRYING OUT THE INVENTION

Figure 1:
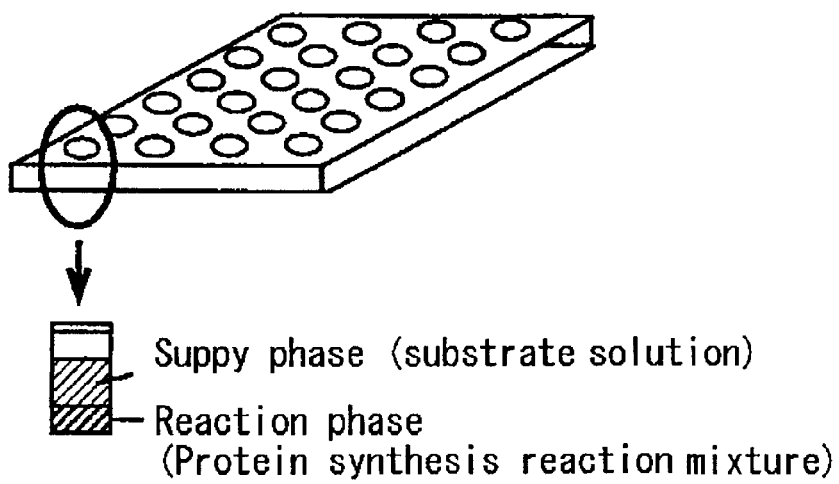
FIG. 1 illustrates an example of the multilayered method for diffusion continuous batch cell-free protein synthesis. The part surrounded by the leader line illustrates a cross section of a well of a titre plate.

One embodiment of the present invention is a diffusion continuous batch cell-free protein-synthesis method that consists of a synthesis reaction mixture containing a biological extract (reaction phase) and a substrate and energy source solution (supply phase), and is characterized by:
1) continuously supplying substrate and energy source molecules in the supply phase to the reaction phase by the free diffusion via interface by directly contacting without barrier such as semipermeable membrane and ultrafiltration membrane,
2) transferring by-products formed in the reaction phase into the supply phase at the same time as the above supply, and
3) prolonging the reaction lifetime by the transfer to enhance the efficiency of the synthesis reaction.

The interface between both phases can be formed vertically or horizontally in the above diffusion continuous batch cell-free protein-synthesis method. In order to horizontally form the interface, for example, the reaction phase is added to a reaction vessel to form a lower layer, and then the supply phase can be gently overlayed on the reaction phase without disturbing the interface (see FIG. 1). Any reaction vessel can be used for this purpose as long as the vessel has a shape and a size that give a sufficient diffusion rate for solutes in the interface. Although tubes and multi-well microtitre plates can be used as such reaction vessels, others can also be used. In addition, the interface between the two phase can be vertically formed by overlaying a synthesis reaction mixture (reaction phase) on a supply solution (supply phase), followed by centrifuging a reaction vessel containing these. The larger an area of the interface between both phases becomes, the larger a mass-exchange rate by the diffusion and a protein-synthesis efficiency become. Therefore, the optimal volume ratio of the reaction phase to the supply phase depends on the area of the interface between both phases. Although any (reaction phase: supply phase) volume ratio can be used, in case the interface is a circle and has a diameter of 7 mm, the (reaction phase:supply phase) volume ratio is preferably between (1:4) and (1:8), more preferably (1:5).

The synthesis reaction mixture containing the above reaction phase contains a biological extract necessary for the cell-free protein-synthesis reaction and a desired mRNA to be a template for the protein synthesis, and has a composition used for the conventionally known batch cell-free protein-synthesis system. For the biological extract, well-known biological extracts that have been used for the conventional cell-free protein-synthesis method can be used such as wheat embryo extract, *Escherichia coli* extract, and rabbit reticulocyte extract. These extracts can be prepared according to well-known methods. A wheat embryo extract is preferably prepared according to the method described in Madin K., et al., Proc. Natl. Acad. Sci. USA (2000), 97, 559–564 (WO00/68412). The synthesis reaction mixture contains a biological extract, for example, at 48%(v/v) per total volume (200 $A_{260\,nm}$ units/ml) in case a wheat embryo extract is used as the biological extract, and has the following composition (final concentration): 1,000 units/ml ribonuclease inhibitor (RNAsin), 30 mM HEPES-KOH (pH 7.6), 95 mM potassium acetate, 2.65 mM magnesium acetate, 2.85 mM dithiothreitol, 0.5 mg/ml creatine kinase, 1.2 mM adenosine triphosphate (ATP), 0.25 mM guanosine triphosphate (GTP), 16 mM creatine phosphate, 0.380 mM spermidine, 0.3 mM each of twenty L-type amino acids, 0.05% NP-40, and 600 µ/ml mRNA. The composition of the synthesis reaction mixture is not limited to the above composition. Any composition can be used as long as the cell-free protein-synthesis reaction efficiently progresses. For example, instead of the above mRNA, mRNA is synthesized by a transcription reaction mixture containing a plasmid (encoding the target gene), RNA polymerase, nucleotides, and so on, and the composition of the transcription reaction mixture is changed by the gel filtration method and/or the dialysis method to one suitable for the translation, and the obtained solution can be used as the synthesis reaction mixture (see Example 1 below).

The above composition of the synthesis reaction mixture can be properly changed depending on the kind of the biological extract to use. When *Escherichia coli* is used as the biological extract, a protein-synthesis reaction mixture can be prepared by the method described by Pratt, J. M. [Transcription and Translation (1984), 179–209, Hames, B. D. & Higgins, S. J., eds. IRL Press, Oxford] using an *E. coli* extract prepared according to the literature. For example, a transcription reaction mixture is prepared that contains an *E. coli* extract at 50%(v/v), and has the following composition (final concentration): 57 mM HEPES-KOH (pH 8.2), 75 mM potassium acetate, 36 mM ammonium acetate, 16 mM magnesium acetate, 1.7 mM dithiothreitol, 0.3 U/ml pyruvate kinase, 0.17 mg/ml *E. coli* tRNA mixed solution, 34 mg/ml L-5-formyl-5,6,7,8-tetrahydrofolic acid, 6.7 µg/ml plasmid (encoding the target gene), 33 µ/ml T7 RNA polymerase, 1.2 mM ATP, 0.85 mM GTP, 0.85 mM UTP, 0.85 mM CTP, 56 mM phosphoenolpyruvate, and 0.2 mM each of twenty L-type amino acids to synthesize a mRNA, and then the composition of the obtained transcription reaction mixture is changed by the gel filtration method and/or the dialysis method to a mixture having a composition suitable for the translation reaction, and the obtained solution can be used as the synthesis reaction mixture (see Example 1 below).

In the case of a cell-free protein-synthesis system using an *E. coli* extract, an mRNA is synthesized with a transcription reaction mixture as described above, and a supply solution is overlayed onto the transcription reaction mixture, and then a protein synthesis reaction can be carried out under a stationary condition at a temperature suitable for the translation reaction. The composition of the synthesis reaction mixture is not limited to the above composition, but any composition can be used as long as the cell-free protein-synthesis reaction efficiently progresses. For example, a synthesis reaction mixture having a composition suitable for the translation reaction can be prepared by properly adding an mRNA encoding the target gene prepared according to a well-known method (Gurevich, V. V., (1996) Methods in Enzymology, 275, 383–397) instead of plasmid (encoding the target gene), T7 RNA polymerase, UTP, and CTP in the above transcription reaction mixture.

In addition, the protein synthesis reaction can be further stabilized by adding a sugar alcohol such as inositol, xylitol and/or ficoll to the above synthesis reaction mixture to elevate the viscosity or density of the synthesis reaction mixture to control the mixing rate between the reaction phase and the supply phase.

Moreover, the supply solution forming the above supply phase contains substrates and energy sources (e.g., amino acids, ATP, GTP, creatine phosphate), other ions necessary for the protein synthesis, and a buffer. For example, in case the above protein synthesis reaction mixture containing a wheat embryo extract is used as the reaction phase, a supply solution containing 30 mM HEPES-KOH (pH 7.6), 95 mM potassium acetate, 2.65 mM magnesium acetate, 2.85 mM dithiothreitol, 1.2 mM ATP, 0.25 mM GTP, 16 mM creatine phosphate, 0.380 mM spermidine and 0.3 mM each of twenty L-type amino acids can be used. In case the above protein-synthesis reaction mixture containing an *Escherichia coli* extract is used as the reaction phase, for example, a supply solution containing 57 mM HEPES-KOH (pH 8.2), 75 mM potassium acetate, 36 mM ammonium acetate, 16 mM magnesium acetate, 1.7 mM dithiothreitol, 34 mg/ml L-5-formyl-5,6,7,8-tetrahydrofolic acid, 1.2 mMATP, 0.85 mM GTP and UTP and CTP, 56 mM phosphoenolpyruvate, and 0.2 mM each of twenty L-type amino acids, can be used.

The protein synthesis reaction is carried out under a stationary condition at an optimal temperature usually used for various cell-free protein-synthesis reactions. The temperature is from 20° C. to 30° C., preferably 26° C. in case a wheat embryo extract is used as the biological extract, while the temperature is from 30° C. to 37° C., preferably 30° C. in case an *Escherichia coli* extract is used as the biological extract.

In one embodiment of the present invention, in a cell-free protein-synthesis method using a wheat-embryo extract, a synthesis reaction mixture is diluted by adding a diluting solution after the reaction mixture is pre-incubated. Thus, the synthesis-reaction lifetime can be prolonged to enhance the efficiency of the protein synthesis.

In a dilution batch cell-free protein-synthesis method, a conventional batch cell-free protein-synthesis reaction mixture, for example, using a synthesis reaction mixture having the above composition is used, after pre-incubation is carried out for 15 min to 30 min, the protein synthesis is carried out. Then, a wheat-embryo extract contained in the reaction mixture is diluted to 7%–12% or so by adding "a solution having the same composition as the supply solution in the above diffusion continuous protein-synthesis method" containing substrates and energy sources (e.g., amino acids, ATP, GTP, creatine phosphate), other ions necessary for the protein synthesis, and a buffer. Then the reaction is carried out under the conditions. The optimal temperature for the protein synthesis reaction is from 20° C. to 30° C., preferably 26° C. in case a wheat-embryo extract is used. It is known that the stability of enzymes and translation protein factors generally decreases at low concentrations. Therefore, the efficiency of the synthesis reaction can be further enhanced by beforehand adding well-known stabilizer(s) such as inositol, xylitol and ficoll to the synthesis reaction mixture.

Although the above dilution batch protein synthesis method using a wheat-embryo extract was very effective, the effect could not be confirmed with a system using an *Escherichia coli* extract probably due to properties of the wheat-embryo extract.

Moreover, pre-incubation is an extremely important step in this method, and omitting this step reduces the efficiency of the protein synthesis reaction. Therefore, it is considered that a stable translation-initiation complex is formed during the pre-incubation. However, the molecular mechanism concerning this peculiar phenomenon is a future subject.

In addition, one embodiment of the present invention is a batch cell-free protein-synthesis method characterized by:
1) using "a gel-filtration column or semipermeable membrane" for the reaction mixture after the synthesis reaction stops,
2) re-supplying raw materials necessary for the protein synthesis such as substrates and energy sources necessary for the protein synthesis (e.g., amino acids, ATP, GTP, creatine phosphate), 3) at the same time as (2), removing by-products formed during the reaction from the reaction mixture, and
4) enhancing the efficiency of the synthesis reaction.

This method is a batch method comprising discontinuous steps of the protein-synthesis reaction, the supply of substrates and energy sources to the reaction mixture, and the removal of by-products. This method is fundamentally different from the continuous cell-free protein-synthesis method according to Spirin et al.

In this discontinuous batch cell-free protein-synthesis method, 1) a conventional batch cell-free protein-synthesis reaction is initiated using a reaction vessel such as test tube, 2) the protein-synthesis reaction is completely stopped by chilling the reaction mixture down to 0° C. to 4° C. after the synthesis reaction stopped, and 3) the reaction mixture after the reaction stop is treated with the column chromatography using gel filtration particles (e.g., Sephadex G-25) for separating low-molecular compounds beforehand equilibrated with a solution containing substrates and energy sources such as amino acids, ATP, GTP, and creatine phosphate. For the equilibration, a solution having the same composition as the supply solution in the above diffusion continuous batch protein-synthesis method can be used.

By the above gel-filtration procedure, by-products are trapped in Sephadex particles, and a cell-free protein-synthesis reaction mixture exchanged with fresh amino acids, ATP, GTP, and creatine phosphate is regenerated in a void fraction. Incubating the regenerated solution again permits initiating the translation reaction, and the protein-synthesis reaction progresses for several hours. In case the synthesis reaction is stopped again, the above gel-filtration procedure is repeated. By repeating this procedure, the synthesis reaction that is stopped in a short time by a usual batch method can be continued for a long time to enhance the protein-synthesis yield.

Moreover, even if the dialysis method is used instead of the above gel-filtration method for "the re-supply of substrates and energy sources" and "the removal of by-products" in the above discontinuous batch cell-free protein-synthesis method, a similar effect or higher is obtained.

As described above, the batch method according to the present invention is:
1) a diffusion continuous batch method using a reaction phase consisting of a synthesis reaction mixture containing a cell-free extract and a supply phase consisting of a substrate- and energy-source-supplying solution containing amino acids, ATP, GTP, and creatine phosphate, wherein a) the reaction phase and the supply phase are directly contacted each other to continuously supply substrates and energy sources into the reaction phase by the free diffusion via the interface, and b) at the same time as the above supply, by-products formed in the reaction phase are transferred into the supply phase,
2) a dilution batch method by reducing the concentration of the cell extract contained in the synthesis reaction mixture in a cell-free protein-synthesis system using a wheat embryo extract, and
3) a discontinuous batch method by using the gel-filtration method or the dialysis method after the protein-synthesis reaction is stopped, wherein a) substrates and energy sources such as amino acids, ATP, GTP, and creatine phosphate necessary for the protein synthesis are re-supplied to the synthesis reaction mixture, and b) at the same time as the above re-supply, by-products formed during the reaction are discontinuously removed.

The above batch method according to the present invention is extremely effective as a cell-free protein-synthesis method different from the conventional continuous batch cell-free protein-synthesis method.

These methods can be carried out singly or in a combination. For example, the combination of the diffusion continuous batch method and the discontinuous batch method or the combination of the dilution batch method and the discontinuous batch method can be carried out for enhancing the efficiency of the protein synthesis. Moreover, the concentration of a cell or tissue extract to initially add can be elevated to carry out the combination of the above three methods.

In addition, the present invention permitted prolonging the lifetime of the cell-free protein-synthesis reaction, hence remarkably enhancing the efficiency of the protein synthesis compared with the conventional batch method, and establishing the cell-free protein-synthesis method having a performance comparable or more to the continuous cell-free protein-synthesis method, using a semipermeable membrane, established by Spirin et al. [Spirin, A, et al., (1993) Methods in Enzymology, 217, 123–142].

EXAMPLES

Although the present invention is described in more detail citing examples below, the present invention is not limited to the examples below.

Example 1

As an example of a diffusion continuous batch cell-free protein-synthesis method, the protein synthesis was carried out using a wheat-embryo extract by the multi-layered diffusion continuous batch method as illustrated in FIG. 1.

The wheat embryo extract was prepared according to Madin K. et al. [Proc. Natl. Acad. Sci. USA (2000), 97, 559–564; WO00/68412].

Figure 6:
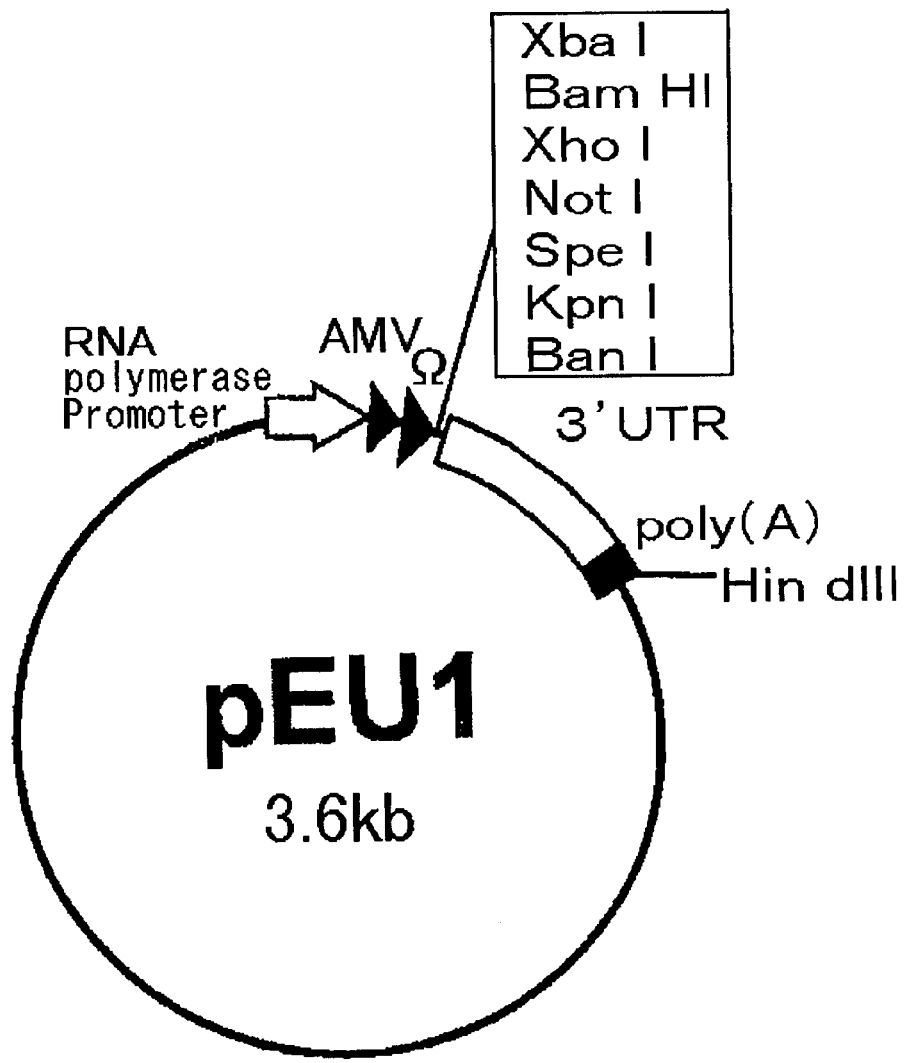
FIG. 6 illustrates the structure of plasid pEU1 that can be generally used.

In addition, in order to synthesize an mRNA to be a translation template in the wheat-embryo cell-free protein-synthesis reaction, general plasmid pEU1 constructed by Endo (FIG. 6) (WO01/27260) was used. As a gene encoding the target protein, jellyfish green-fluorescent-protein (GFP) gene (gfp gene) was used, and was inserted into the above plasmid according to the conventional method. The obtained plasmid was cut with HindIII to give a linear form, which was used as a translation template to synthesize an mRNA according to the conventional method. The synthesized mRNA does not have CAP at 5'-end, has AMV-Ω sequence at 5'-end as non-translation sequence, and has 500 bases derived from the plasmid at 3'-end. The above AMV-Ω sequence is a base sequence obtained by serially linking 5'-end leader structure of alfalfa mosaic virus mRNA (AMV-mRNA) to 5'-end Ω sequence of tobacco mosaic virus mRNA (TMV-mRNA) (WO01/27260). The addition of these non-translation sequence enhances the stability of the RNA, so that the use of this mRNA enhances the efficiency of the cell-free protein synthesis. Moreover, the use of an mRNA having CAP at 5'-end also gave the result similar to one below.

Then, a protein-synthesis reaction mixture that contains 48%(v/v) wheat-embryo extract (concentration of 200 $A_{260\ nm}$ units/ml), 1,000 units/ml ribonuclease inhibitor (RNAsin) (Takara Bio Inc.), 30 mM HEPES-KOH (pH 7.6), 95 mM potassium acetate, 2.65 mM magnesium acetate, 2.85 mM dithiothreitol, 0.5 mg/ml creatine kinase, 1.2 mM adenosine triphosphate (ATP), 0.25 mM guanosine triphosphate (GTP), 16 mM creatine phosphate, 0.380 mM spermidine, 0.3 mM each of twenty L-type amino acids, 0.05% NP-40, and 600 µg/ml mRNA, was prepared. In order to assay the amount of protein synthesized, 4 μCi of $^{14}$C-leucine (300 mCi/mmol) was added per 1 ml of the above protein synthesis reaction mixture [Proc. Natl. Acad. Sci. USA (2000), 97, 559–564].

This protein-synthesis reaction mixture was added to reaction vessels having a bore of 7 mm (microtitre plate), 5 mm (1.5-ml test tube), and 3 mm (0.2-ml test tube), and 5 times volumes of supply solution [30 mM HEPES-KOH (pH 7.6), 95 mM potassium acetate, 2.65 mM magnesium acetate, 2.85 mM dithiothreitol, 1.2 mM ATP, 0.25 mM GTP, 16 mM creatine phosphate, 0.380 mM spermidine and 0.3 mM each of twenty L-type amino acids] were overlayed on the reaction mixture gently without disturbing the interface, and the resultant preparation was incubated under a stationary condition at 26° C. for 3, 6, 9, or 17 h to carry out the protein synthesis reaction. The amount of proteins synthesized was assayed using the incorporation of a radio isotope into a trichloroacetic acid-insoluble fraction as an index according to the conventional method, and the synthesized proteins were visualized by the autoradiography (Endo, Y. et al., (1992) J. Biotechnol., 25, 221–2301[Proc. Natl. Acad. Sci. USA (2000), 97, 559–5641. Results are shown in FIG. 2A and FIG. 2B.

As a control, the conventional batch cell-free protein-synthesis method was carried out. In this method, the same mRNA, wheat-embryo extract, and protein-synthesis reaction mixture containing these as those used in the above diffusion continuous batch cell-free protein-synthesis method were used except that the supply solution was not added.

Figure 2:
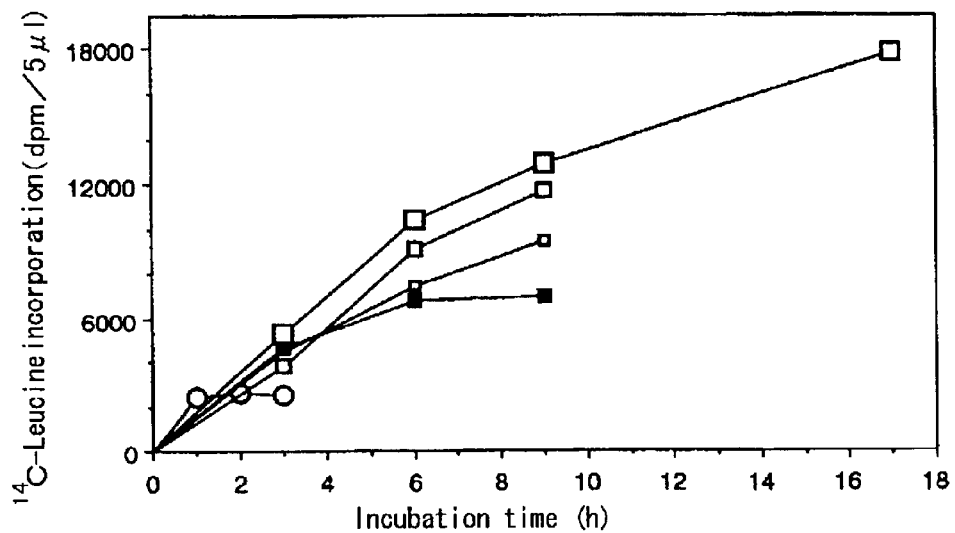
FIG. 2 illustrates the synthesis of green fluorescent protein (GFP) by the diffusion continuous batch cell-free protein synthesis method using a wheat embryo extract.
Figure 2:

As FIG. 2A illustrates, the protein-synthesis reaction stopped 1 h after the initiation of the reaction in the conventional batch method (○). This result is in complete agreement with the results of Endo, Y. et al., (1992) J. Biotechnol., 25, 221–230 and Proc. Natl. Acad. Sci. USA (2000) 97, 559–564.

On the other hand, in the multi-layered method using a reaction vessel having a bore of 7 mm (area of the interface is 0.385 cm$^2$) (□-□, large symbol), the synthesis reaction progressed even 17 h after the initiation of the reaction, the amount synthesized reached 9 times or more that of the conventional batch method. In addition, the influence of the area of the interface between the reaction phase and the supply phase on the synthesis reaction was investigated using reaction vessels having different sizes, the synthesis efficiency in 9 h after the initiation of the reaction was showed that a reaction vessel having a bore of 5 mm (area of the interface was 0.196 cm$^2$) (□-□, middle symbol) was 91% as compared with that of 7 mm, a reaction vessel having a bore of 3 mm (area of the interface was 0.071 cm$^2$) (□-□, small symbol) was 75% as compared with that of 7 mm.

The autoradiogram shown in FIG. 2B completely supported the experimental result obtain in the investigation of the amount of protein synthesized as measured by $^{14}$C-leucine incorporation shown in FIG. 2A with respect to both "the synthesis reaction lifetime transient of proteins" and "molecular weight of synthesis products and amount thereof" in the conventional batch method and the diffusion continuous batch method. The diffusion continuous batch method is displayed as 'the overlay method' in FIG. 2B. Moreover, the protein synthesis results by the diffusion continuous batch method are shown with respect only to results using reaction vessels having a bore of 7 mm.

Similar results were obtained also in case of synthesizing an mRNA with a transcription reaction solution according to the transcription-translation all-in-one protein-synthesis method shown in Reference Example 1 below, following by changing the composition of the transcription reaction mixture to a solution having a composition suitable for the translation reaction by the gel-filtration method and/or the dialysis method, the obtained solution was used as a synthesis reaction mixture according to a manner similar to that described above in protein synthesis.

The above results showed that 1) the diffusion continuous batch protein synthesis method using a wheat embryo extract gives a remarkably high synthesis efficiency compared with the conventional bath method, that 2) the larger the area of the interface between the reaction phase and the supply phase is, the higher the synthesis efficiency is, and that 3) the increase in the synthesis yield by the method is due to the prolongment of the synthesis-reaction lifetime.

Example 2

As one example of the dilution batch cell-free protein-synthesis method, the protein-synthesis reaction was carried out by carrying out a pre-incubation using a protein-synthesis reaction mixture containing the wheat embryo extract prepared in Example 1 and an mRNA encoding GFP by the conventional batch method at 26° C. for 15 min, adding five times volumes of the diluting solution to the resultant mixture, followed by further incubating the diluted mixture at 26° C. for 3, 6, or 9 h, wherein the diluting solution had the same composition as the supply solution prepared in Example 1, wherein the amount of protein synthesized was assayed in a manner similar to that of Example 1. Results are shown in FIG. 2A (■-■) and FIG. 2B.

As FIG. 2A shows, compared with the conventional batch method in which the synthesis reaction stops within 1 h (○-○), in case the cell-free protein synthesis was carried out by the dilution batch method, the synthesis reaction linearly progressed for 6 h after the initiation of the reaction (■-■).

The autoradiogram shown in FIG. 2B completely supported the experimental results obtained in the investigation of the amount of the protein synthesized as measured by the $^{14}$C-leucine incorporation shown in FIG. 2A.

Although this dilution batch cell-free protein-synthesis method gives a lower synthesis yield than that of the diffusion continuous batch method shown in Example 1, the amount of the protein synthesized by the dilution batch cell-free protein synthesis method was about three times that of the conventional batch method, and the dilution batch cell-free protein-synthesis method showed a significantly high synthesis efficiency.

Similar results were obtained also in case of synthesizing an mRNA with a transcription reaction solution according to the transcription-translation all-in-one protein-synthesis method shown in Reference Example 1 below, following by changing the composition of the transcription reaction mixture to a solution having a composition suitable for the translation reaction by the gel-filtration method and/or the dialysis method, the obtained solution was used as a synthesis reaction mixture according to a manner similar to that described above in protein synthesis.

Moreover, in case the pre-incubation reaction procedure was omitted in the above dilution batch cell-free protein-synthesis method, the above remarkable prolongment of the synthesis-reaction lifetime was not observed. In addition, with respect to the cell-free protein-synthesis system using an *Escherichia coli* extract, the effect of the dilution batch method was not recognized.

As described above, it was demonstrated that the dilution batch cell-free protein-synthesis method is also an effective protein-synthesis means with respect to the cell-free protein-synthesis system using a wheat-embryo extract.

Example 3

It was demonstrated that a dihydrofolate reductase (DHFR) derived from *Escherichia coli* can be synthesized in addition to GFP synthesized in Example 1 by the diffusion continuous batch cell-free protein-synthesis method, and it was confirmed that this method is effective for the synthesis of general protein molecule species.

Figure 3:
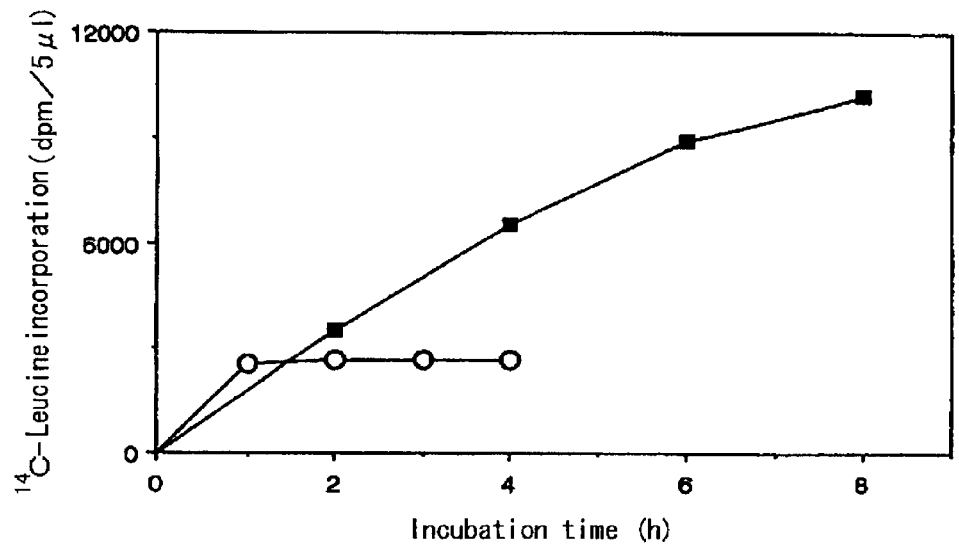
FIG. 3 illustrates the synthesis of dihydrofolate reductase (DHFR) by the diffusion continuous batch cell-free protein synthesis method using a wheat embryo extract.
Figure 3:
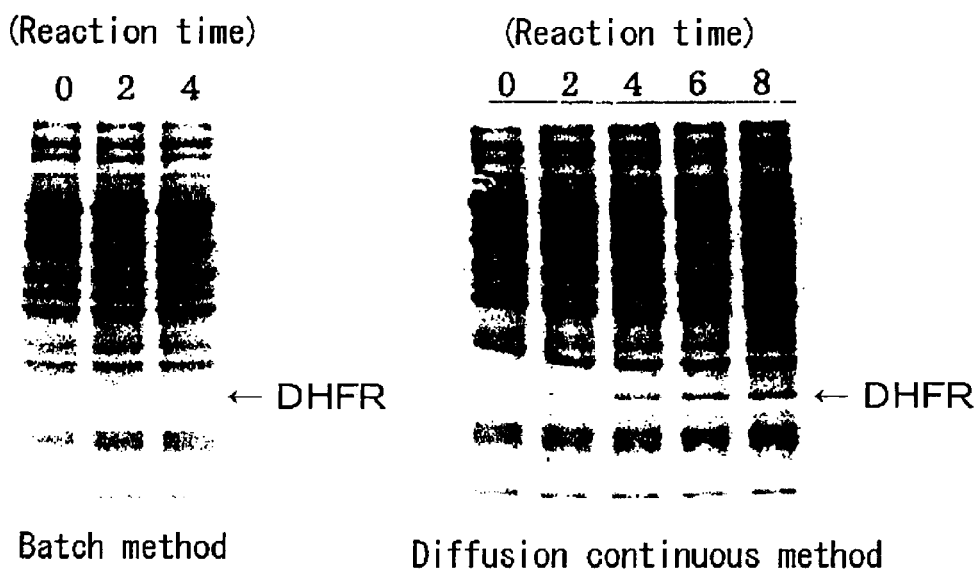

The protein synthesis was carried out in a manner similar to Example 1 using a protein-synthesis solution having a composition similar to that of Example 1 except that the mRNA was an mRNA encoding DHFR, giving the results shown in FIG. 3. The amounts of proteins synthesized were assayed using the incorporation of the radio isotope into a trichloroacetic acid-insoluble fraction as an index according to the conventional method, and proteins synthesized were identified by the SDS-polyacrylamide-gel electrophoresis and the staining with Coomassie Brilliant Blue (CBB) [Endo, Y. et al., (1992) J. Biotechnol., 25, 221–230][Proc. Natl. Acad. Sci. USA (2000) 97, 559–564].

As shown in FIG. 3A, also in the DHFR synthesis, the synthesis reaction by the diffusion continuous batch cell-free protein-synthesis method (■-■) significantly continued longer than that of the conventional batch method (o-o). Results of the analysis of the lifetime of the synthesis reaction and the amounts of synthesis products by the SDS-polyacrylamide-gel electrophoresis [arrows in FIG. 3B show bands of DHFR stained with Coomasie Brilliant Blue] completely supported the results shown in FIG. 3A. The measurement of the band staining intensity of synthesized DHFR demonstrated that the diffusion continuous batch cell-free protein-synthesis method permitted synthesizing 0.9 mg DHFR per 1 ml of reaction volume for 8 h.

Example 4

It was demonstrated by using an *Escherichia coli* extract that the diffusion continuous batch cell-free protein-synthesis method is generally effective even for a cell-free protein-synthesis system using a cell extract prepared from any biological species.

The *Escherichia coli* extract was prepared according to Pratt, J. M., Transcription and Translation (1984), 179–209, Hames, B. D. & Higgins, S. J., eds, IRL Press, Oxford. In this example, a mRNA was first synthesized by the transcription-translation all-in-one cell-free protein-synthesis system (see Reference Example 1), and then the composition of the transcription reaction mixture containing the mRNA was changed to a composition suitable for the translation reaction by the gel filtration method, and the resultant mixture was added to a reaction vessel, and a supply solution was overlayed onto the mixture in a manner similar to Example 1, and the obtained preparation was incubated under a stationary condition at 30° C. to carry out the protein synthesis.

An mRNA was synthesized by preparing an *Escherichia coli* cell-free protein-synthesis reaction mixture that contains an *E. coli* extract at 50%(v/v) and has the following composition (final concentration): 57 mM HEPES-KOH (pH 8.2), 75 mM potassium acetate, 36 mM ammonium acetate, 16 mM magnesium acetate, 1.7 mM dithiothreitol, 0.3 U/ml pyruvate kinase, 0.17 mg/ml *E. coli* tRNA mixed solution, 34 mg/ml L-5-formyl-5,6,7,8-tetrahydrofolic acid, 6.7 µg/ml plasmid (encoding GFP gene), 33 µg/ml T7 RNA polymerase, 1.2 mM ATP, 0.86 mM GTP and UTP and CTP, 56 mM phosphoenolpyruvate, and 0.3 mM each of twenty L-type amino acids, followed by incubating the resultant mixture at 30° C. for 90 min. Then, the composition of the above reaction mixture was changed to a composition suitable for the translation reaction by the gel filtration method, and then 25 µl of the obtained mixture was transferred to a reaction vessel (microtitre plate having a bore of 7 mm), and the supply solution having the following composition was gently overlaid, and the obtained preparation was incubated at 30° C. to carry out the protein synthesis. In case the protein synthesis was measured using the incorporation of an amino acid as index, 4 µCi of $^{14}$C-leucine (300 mCi/mmol) was added to 1 ml of the above reaction mixture.

The plasmid to be the transcription template of an mRNA was prepared by replacing RAS gene of pK7-RAS [Kigawa, T., et al., (1995) J. Biomol. NMR, 6, 129–134] having T7-phage promoter sequence with jelly fish GFP gene.

The composition of the supply solution used for the *Escherichia coli* cell-free protein synthesis system was as follows (final concentration): 57 mM HEPES-KOH (pH 8.2), 75 mM potassium acetate, 36 mM ammonium acetate, 16 mM magnesium acetate, 1.7 mM dithiothreitol, 34 mg/ml L-5-formyl-5,6,7,8-tetrahydrofolic acid, 1.2 mM ATP, 0.85 mM GTP and UTP and CTP, 56 mM phosphoenolpyruvate, and 0.2 mM each of twenty L-type amino acids. In case the protein synthesis was measured using the incorporation of an amino acid as index, 4 µCi of $^{14}$C-leucine (300 mCi/mmol) was added to 1 ml of the above reaction mixture.

Figure 4:
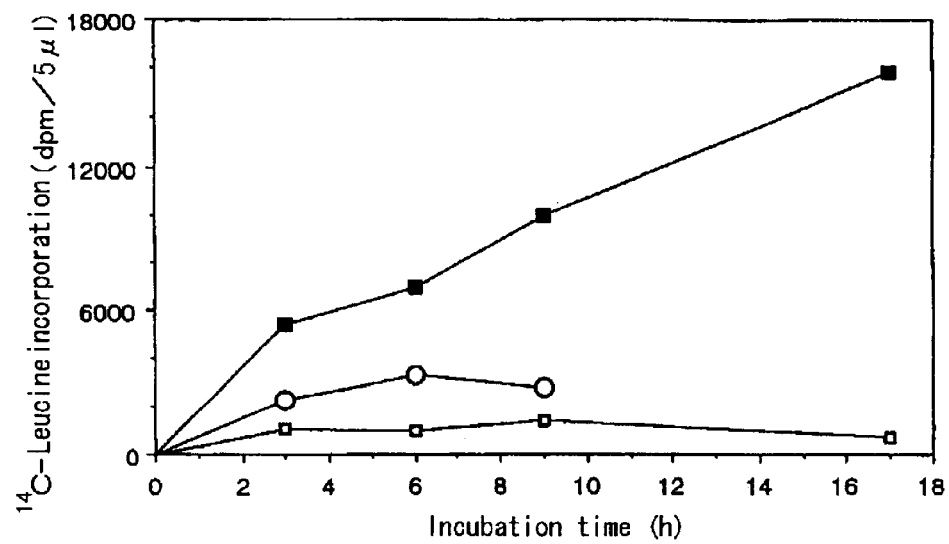
FIG. 4 illustrates the synthesis of GFP by the diffusion continuous batch cell-free protein synthesis method using an *Escherichia coli* extract.
Figure 4:
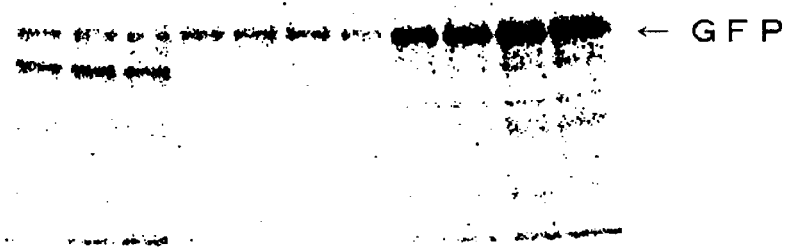

FIG. 4A illustrates results of the protein synthesis as measured by the incorporation of $^{14}$C-leucine. GFP synthesis reaction by the conventional batch method (o-o) completely stopped 3 h after the initiation of the reaction, while that of the diffusion continuous batch cell-free protein-synthesis method (■-■) lasted for 17 h after the initiation of the reaction. The amount of synthesized protein as calculated from the amount of incorporated amino acid in the diffusion continuous cell-free protein synthesis method reached 4 times or more that of the batch method. Results of the analysis of the time transient of the synthesis reaction and molecular weights and synthesis amounts of synthesis products by the autoradiogram shown in FIG. 4B completely supported results of FIG. 4A. On the other hand, in the control experiment in which both phases were mixed by a vortex mixer just after the above supply solution (supply phase) was overlayed onto the above protein-synthesis reaction mixture (reaction phase), the protein synthesis was significantly reduced compared with the conventional batch method.

This fact is in complete agreement with the result that increasing the concentration of a cell-free extract in the reaction mixture with respect to the *Escherichia coli* cell-free protein synthesis system is important for enhancing the efficiency [Kim, D. M., (1996) Eur. J. Biochem. 239, 881–886]. This result clearly shows that the prolongment of the lifetime of the protein-synthesis reaction observed in the diffusion continuous batch method is not due to, for example, the reduction of the reaction rate by the reduction of the concentration of a component necessary for the protein synthesis in the reaction mixture, such as, ribosome, but due to the intrinsic property of the diffusion continuous batch cell-free protein synthesis method.

In addition, results similar to those described above were obtained also by synthesizing an mRNA by the transcription-translation all-in-one cell-free protein synthesis system (see Reference Example 1) using an *Escherichia coli* extract, overlaying the supply solution onto the reaction mixture in a manner similar to Example 1, followed by carrying out the protein-synthesis reaction under a stationary condition at 30° C.

Example 5

An example of the cell-free protein-synthesis method using a wheat embryo by the discontinuous batch method using the gel filtration method is described below. The same protein-synthesis solution as prepared in Example 1 was added to normal small test tubes or a 96-well titre plate, and the obtained preparation was incubated under a stationary condition at 26° C. by a usual method. Under this reaction conditions, the protein synthesis stops within several hours. For example, in case a reaction mixture containing a wheat embryo extract at 48%(v/v) is used, the synthesis reaction completely stops within 1 h after the initiation of the reaction. This can be confirmed by the measurement of amino acid incorporation into proteins and/or the polyribosome analysis by the sucrose density gradient centrifugation method [Proc. Natl. Acad. Sci. USA (2000) 97, 559–564]. The reaction mixture after the above synthesis reaction stopped was treated with the gel filtration using a Sephadex G-25 column beforehand equilibrated with a supply solution containing substrates and energy sources (e.g., amino acids, ATP, GTP), other ions necessary for the protein synthesis reaction, and a buffer, and the protein synthesis was carried out again at 26° C., wherein the supply solution had a composition similar to that of Example 1.

Figure 5:
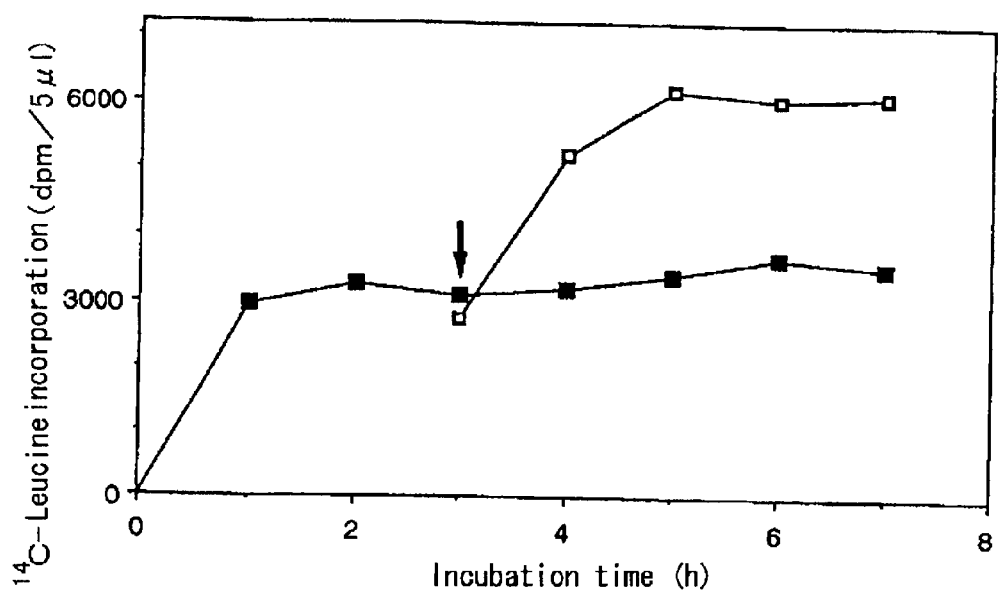
FIG. 5 illustrates the synthesis of GFP by the discontinuous gel-filtration batch cell-free protein-synthesis method using a wheat embryo extract (□-□) or without gel filtration (■-■). The arrow indicates the time when the reaction mixture was treated with the gel filtration.

As the result of $^{14}$C-leucine incorporation in FIG. 5 shows, the synthesis reaction by the conventional batch method completely stopped within 1 h after the initiation of the reaction (■-■). However, the gel filtration as described above 3 h after the initiation of the reaction (arrow in FIG. 5) and the subsequent incubation permitted the restart of the protein synthesis reaction (□-□). In addition, the velocity gradient of $^{14}$C-leucine incorporation was almost equal to that in the early stage of the reaction. Therefore, it was found that the efficiency of the protein synthesis after the gel filtration was at a level comparable to that in the early stage of the reaction.

Similar results were obtained also in case of synthesizing an mRNA with a transcription reaction solution according to the transcription-translation all-in-one protein-synthesis method shown in Reference Example 1 below, following by changing the composition of the transcription reaction mixture to a solution having a composition suitable for the translation reaction by the gel-filtration method and/or the dialysis method, the obtained solution was used as a synthesis reaction mixture according to a manner similar to that described above in protein synthesis.

Since the above cell-free protein-synthesis system using a wheat-embryo extract is extremely stable [Endo, Y. et al., (1992) J. Biotech., 26, 221–230] [Proc. Natl. Acad. Sci. USA (2000) 97, 559–564], it is possible to keep the reaction time for a long time by repeating the gel filtration procedure. Therefore, the above discontinuous batch cell-free protein-synthesis method is useful as an efficient protein synthesis method, for example, in a cell-free protein-synthesis system using a wheat-embryo extract.

Reference Example 1

The transcription-translation all-in-one protein-synthesis method permits synthesizing an m-RNA with the transcription reaction mixture, then changing the composition of the transcription reaction-mixture to one suitable for the translation reaction by the gel filtration method and/or the dialysis method, and using the obtained mixture as the synthesis reaction mixture.

First, a transcription reaction mixture consisting of a template DNA, four kinds of substrate ribonucleoside-5'-triphosphate, and if necessary, CAP molecule, RNA polymerase, spermidine, magnesium ion, and an appropriate buffer [80 mM HEPES-KOH (pH 7.6), 16 mM magnesium acetate, 2 mM spermidine, 10 mM dithiothreitol, 2.5 mM ATP, 2.5 mM GTP, 2.5 mM CTP, 2.5 mM UTP, 1U/µl ribonuclease inhibitor, 3 U/µl SP6 RNA polymerase (Takara Bio., Inc)] was added to a gel filter-installed spin column as the reaction vessel. An mRNA is continuously synthesized by the dialysis using an outer solution, for the dialysis, which has the same composition as the above transcription reaction mixture except template DNA, RNA polymerase, and ribonuclease inhibitor.

After the synthesis of the mRNA, the spin column is centrifuged at a low speed, and the composition of the above transcription reaction mixture is changed to one suitable for the translation reaction by the gel filtration procedure using the protein synthesis solution (not containing mRNA) as shown in Example 1.

INDUSTRIAL APPLICABILITY

The above cell-free protein-synthesis method according to the present invention does not require complicated techniques such as the ultrafiltration method and dialysis-membrane method using a semipermeable membrane and the column chromatography using a resin to which a translation template was fixed [Spirin, A., et al., (1993) Methods in Enzymology, 217, 123–142]. Therefore, it was shown that the above cell-free protein synthesis method according to the present invention permits efficiently synthesizing a protein in a cell-free system using a tissue/cell extract by any means by introducing one of three techniques for making the synthesis reaction efficient into the conventional batch method.

The above cell-free protein synthesis method according to the present invention does not have faults such as weakness of the material strength of the membrane, decrease in the membrane function due to the clogging, and complexity of the operation, which are observed in the conventional continuous cell-free protein synthesis method using a membrane. Thus, the above cell-free protein-synthesis method according to the present invention permits carrying out the protein synthesis at a considerably high efficiency compared with the conventional method. Therefore, the above technique according to the present invention would be a fundamental element technology, for the automation of the production of a gene product (protein), which is the base for the functional analysis and the structural analysis of a great number of genes that would be provided till the future completion of the genome project, in particular be an essential element technology for the automation of the cell-free protein-synthesis system such as development of full-automatic cell-free protein-synthesis robot for polyspecimen.

What is claimed is:

1. A cell-free protein-synthesis method using a diffusion continuous batch system that includes a synthesis reaction mixture (reaction phase) containing a biological extract and a supply solution (supply phase) containing substrates and energy sources, the method comprising the steps of:
   1) bringing the two phases into direct contact with each other absent a membrane between the two phases to cause a free diffusion via the direct contact interface between the two phases, and continuously supplying substrates and energy source molecules in the supply phase to a translation reaction system in the reaction phase; and 2) removing by-products formed in the reaction phase.

2. A cell-free protein-synthesis method according to claim 1, wherein the biological extract is a wheat-embryo extract.

3. A cell-free protein-synthesis method according to claim 1, wherein the biological extract is an *Escherichia coli* extract.

4. A cell-free protein-synthesis method according to claim 1, wherein by-products formed in the reaction phase are removed from the reaction phase and transferred to the supply phase, thereby diluting said by-products of the reaction phase.

5. A cell-free protein-synthesis method according to claim 1, wherein the direct interface formed between the reaction phase and the supply phase is a vertical plane.

6. A cell-free protein-synthesis method adapted to prolong the lifetime of the synthesis reaction, and enhance the efficiency of the synthesis reaction, comprising the steps of:

pre-incubating a cell-free protein-synthesis reaction mixture (reaction phase) containing a wheat-embryo extract;

adding a substrate and energy source-supplying solution (supply phase) to dilute the cell-free protein-synthesis reaction mixture containing a wheat-embryo extract;

bringing the two phases into direct contact with each other absent a membrane between the two phases to cause a free diffusion via the direct contact interface between the two phases and continuously supplying substrates and energy source molecules in the supply phase to a translation reaction system in the reaction phase; and removing by-products formed in the reaction phase.

7. A batch cell-free protein-synthesis method comprising the steps of:

1) treating a reaction after stopping the synthesis reaction with a gel-filtration column or a semipermeable membrane;

2) re-supplying raw materials and energy sources such as amino acids, ATP, GT and creatine phosphate which are necessary for the protein synthesis; and 3) simultaneously with the re-supply, removing by-products formed during the reaction from the reaction mixture.

8. The batch cell-free protein-synthesis method of claim 7, wherein steps 1)–3) are repeated at least once.

* * * * *

UNITED STATES PATENT AND TRADEMARK OFFICE
CERTIFICATE OF CORRECTION

PATENT NO.    : 6,869,774 B2  
DATED         : March 22, 2005  
INVENTOR(S)   : Endo et al.

Page 1 of 1

It is certified that error appears in the above-identified patent and that said Letters Patent is hereby corrected as shown below:

Column 16,
Line 17, "GT" should read -- GTP --.

Signed and Sealed this

Seventh Day of June, 2005

JON W. DUDAS
*Director of the United States Patent and Trademark Office*

UNITED STATES PATENT AND TRADEMARK OFFICE
CERTIFICATE OF CORRECTION

PATENT NO.        : 6,869,774 B2                                         Page 1 of 1
APPLICATION NO.   : 10/344803
DATED             : March 22, 2005
INVENTOR(S)       : Endo et al.

It is certified that error appears in the above-identified patent and that said Letters Patent is hereby corrected as shown below:

<u>Drawings,</u>
Fig. 1, "Supply" should read -- Supply --.

<u>Column 2,</u>
Line 36, "mixture reaction phase)" should read -- mixture (reaction phase) --.

<u>Column 16,</u>
Line 13, "a reaction" should read -- a reaction mixture --.

Signed and Sealed this

Fourth Day of July, 2006

JON W. DUDAS
*Director of the United States Patent and Trademark Office*

UNITED STATES PATENT AND TRADEMARK OFFICE
CERTIFICATE OF CORRECTION

PATENT NO. : 6,869,774 B2  Page 1 of 1
APPLICATION NO. : 10/344803
DATED : March 22, 2005
INVENTOR(S) : Endo et al.

It is certified that error appears in the above-identified patent and that said Letters Patent is hereby corrected as shown below:

On the title page: item
(73) Assignee: "Yaeta Endo, Ehime (JP)" should read --CellFree Sciences Co., Ltd., Kanagawa, Japan--.

Signed and Sealed this

First Day of May, 2007

JON W. DUDAS
*Director of the United States Patent and Trademark Office*